United States Patent [19]

Mayrand

[11] Patent Number: 5,691,146
[45] Date of Patent: Nov. 25, 1997

[54] METHODS FOR COMBINED PCR AMPLIFICATION AND HYBRIDIZATION PROBING USING DOUBLY LABELED FLUORESCENT PROBES

[75] Inventor: Paul E. Mayrand, Pacifica, Calif.

[73] Assignee: The Perkin Elmer Corporation, Foster City, Calif.

[21] Appl. No.: 710,075

[22] Filed: Sep. 11, 1996

Related U.S. Application Data

[62] Division of Ser. No. 435,509, May 5, 1995.

[51] Int. Cl.[6] .............. C12Q 1/68; C12Q 1/70; C12P 19/34; C07H 21/04
[52] U.S. Cl. .............. 435/6; 435/5; 435/91.1; 435/91.2; 536/22.1; 536/23.1; 536/24.3; 536/24.31; 536/24.32; 536/24.33; 536/24.5
[58] Field of Search .............. 435/5, 6, 91.1, 435/91.2; 536/24.3, 22.1, 24.31, 24.32, 24.33, 23.1, 24.5

[56] References Cited

U.S. PATENT DOCUMENTS 5,210,015  5/1993  Gelfand et al. .............. 435/6

FOREIGN PATENT DOCUMENTS

WO 93/10267  5/1993  WIPO.

OTHER PUBLICATIONS

Sixou et al, "Intracellular oligonucleotide hybridization detected by fluorescence resonance energy transfer (FRET)", Nucleic Acids Res. 22(4):662–668, 1994.

*Primary Examiner*—W. Gary Jones
*Assistant Examiner*—Jeffrey Fredman
*Attorney, Agent, or Firm*—Paul D. Grossman

[57] ABSTRACT

An oligonucleotide probe is disclosed, the probe including an oligonucleotide, a fluorescer molecule attached to a first end of the oligonucleotide and a quencher molecule attached to the opposite end of the oligonucleotide. The probe is rendered impervious to digestion by the 5'→3' exonuclease activity of a polymerase and the 3'→5' extension of by a polymerase. The invention also includes methods for performing combined PCR amplification and hybridization probing, one such method including the steps of contacting a target nucleic acid sequence with PCR reagents and an oligonucleotide probe as described above, and subjecting these reagents to thermal cycling. One preferred refinement of the above method further includes the addition of a strand displacer to facilitate amplification. Additional similar combined PCR hybridization methods are disclosed, such methods not requiring probes having their 5' ends protected, wherein (i) the polymerase lacks 5'→3' exonuclease activity, (ii) a 5'→3' exonuclease inhibitor is included, and (iii) an exonuclease reactivation step is performed.

10 Claims, 2 Drawing Sheets

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
ATGCCCTCCC  CCATGCCATC  CTGCGT                    26
```

( 2 ) INFORMATION FOR SEQ ID NO: 2:

( i ) SEQUENCE CHARACTERISTICS:
        ( A ) LENGTH: 30 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 2:

```
AGACGCAGGA  TGGCATGGGG  GAGGGCATAC                30
```

( 2 ) INFORMATION FOR SEQ ID NO: 3:

(i) SEQUENCE CHARACTERISTICS:
    (A) LENGTH: 24 nucleotides
    (B) TYPE: nucleic acid
    (C) STRANDEDNESS: single
    (D) TOPOLOGY: linear (xi) SEQUENCE DESCRIPTION: SEQ ID NO: 3:

CGCCCTGGAC TTCGAGCAAG AGAT                                24

(2) INFORMATION FOR SEQ ID NO: 4:

(i) SEQUENCE CHARACTERISTICS:
        (A) LENGTH: 28 nucleotides
        (B) TYPE: nucleic acid
        (C) STRANDEDNESS: single
        (D) TOPOLOGY: linear (xi) SEQUENCE DESCRIPTION: SEQ ID NO: 4:

CCATCTCTTG CTCGAAGTCC AGGGCGAC                            28

(2) INFORMATION FOR SEQ ID NO: 5:

(i) SEQUENCE CHARACTERISTICS:
        (A) LENGTH: 27 nucleotides
        (B) TYPE: nucleic acid
        (C) STRANDEDNESS: single
        (D) TOPOLOGY: linear (xi) SEQUENCE DESCRIPTION: SEQ ID NO: 5:

TCGCATTACT GATCGTTGCC AACCAGT                             27

(2) INFORMATION FOR SEQ ID NO: 6:

(i) SEQUENCE CHARACTERISTICS:
        (A) LENGTH: 31 nucleotides
        (B) TYPE: nucleic acid
        (C) STRANDEDNESS: single
        (D) TOPOLOGY: linear (xi) SEQUENCE DESCRIPTION: SEQ ID NO: 6:

GTACTGGTTG GCAACGATCA GTAATGCGAT G                        31

(2) INFORMATION FOR SEQ ID NO: 7:

(i) SEQUENCE CHARACTERISTICS:
        (A) LENGTH: 28 nucleotides
        (B) TYPE: nucleic acid
        (C) STRANDEDNESS: single
        (D) TOPOLOGY: linear (xi) SEQUENCE DESCRIPTION: SEQ ID NO: 7:

CGGATTTGCT GGTATCTATG ACAAGGAT                            28

(2) INFORMATION FOR SEQ ID NO: 8:

(i) SEQUENCE CHARACTERISTICS:
        (A) LENGTH: 31 nucleotides
        (B) TYPE: nucleic acid
        (C) STRANDEDNESS: single
        (D) TOPOLOGY: linear (xi) SEQUENCE DESCRIPTION: SEQ ID NO: 8:

TTCATCCTTG TCATAGATAC CAGCAAATCC G                        31

METHODS FOR COMBINED PCR AMPLIFICATION AND HYBRIDIZATION PROBING USING DOUBLY LABELED FLUORESCENT PROBES

This application is a division of application No. 08/435,509 filed 05 May 1995, pending.

BACKGROUND

This invention relates generally to the field of nucleic amplification and probing, and more particularly, to methods and compositions for performing PCR and probe hybridization using a single reagent mixture.

Nucleic acid amplification techniques provide powerful tools for the study of genetic material. The polymerase chain reaction (PCR) in particular has become a tool of major importance finding applications in cloning, analysis of genetic expression, DNA sequencing, genetic mapping, drug discovery, criminal forensics, and the like, e.g., Innis et al. in PCR Protocols A guide to Methods and Applications, Academic Press, San Diego (1990); and U.S. Pat. Nos. 4,683,195, 4,683.

For many important applications, in addition to amplifying a target nucleic acid sequence, it is desirable to further characterize such sequence by treatment with a nucleic acid hybridization probe, i.e., a labeled single stranded polynucleotide which is complementary to all or part of the target sequence, e.g., Nucleic Acid Hybridization, Hames et al. Eds., IRL Press, Oxford (1985). Probe hybridization may provide additional sequence selectivity over simple PCR amplification as well as allowing for the characterization of multiple sequence sites within the target nucleic acid sequence in an independent manner.

Traditionally, PCR and probe hybridization processes have been performed as separate operations. However, it is highly desirable to perform both the PCR and the probe hybridization reactions in a combined manner using a single reagent mixture containing both PCR reagents and probing reagents. There are several advantages realized by combining the PCR and the probing process: (i) only a single reagent addition step is required, thereby allowing the combined reactions to proceed without having to open up the reaction tube, thereby reducing the opportunity for sample mix-up and sample contamination; (ii) fewer reagents are needed; (iii) fewer reagent addition steps are required, making automation more straight forward; and, (iv) in the case of in situ methods, there is no requirement to take apart a sample containment assembly used to protect the integrity of the cellular sample during thermocycling.

One existing method which combines PCR with hybridization probing in a single reaction is the technique know as "Taqman", e.g., Holland et al, Proc. Natl. Acad. Sci. USA 88: 7276–7280 (1991). In the Taqman assay, an oligonucleotide probe, nonextendable at the 3' end, labeled at the 5' end, and designed to hybridize within the target sequence, is introduced into the PCR reaction. Hybridization of the probe to a PCR reaction product strand during amplification generates a substrate suitable for the exonuclease activity of the PCR polymerase. Thus, during amplification, the 5'→3' exonuclease activity of the polymerase enzyme degrades the probe into smaller fragments that can be differentiated from undegraded probe. While a significant improvement over prior methods, the Taqman assay has a number of important drawbacks that limit its utility including (i) the requirement that the polymerase enzyme used for the PCR must include a 5'→3' exonuclease activity, (ii) the 5'→3' exonuclease activity must be able to efficiently digest a dye-labeled nucleotide, and (iii) the detectable product of the digestion is a small, rapidly diffusable species which may impact the ability to spatially locate the target sequence when applied to in situ methods.

A second existing method which combines PCR with probing in a single reaction is that disclosed by Higuchi et al. in Biotechnology, 10: 413–417 (1992). In this method, ethidium bromide is added to the PCR reaction and, since the fluorescence of the ethidium bromide increases in the presence of double stranded DNA, an increase in fluorescence can be correlated with the accumulation of double stranded PCR product. However, this method does not provide any sequence specificity beyond the PCR reaction and is limited to the detection of a single sequence site within the target nucleic acid sequence.

A third method which allows for combined amplification and probing steps is that of Bagwell in EP 0601889A2. The probe in Bagwell's method includes a nucleotide sequence which has (i) a segment complementary to the target nucleic acid and (ii) a segment capable of forming one or more hairpins. The probe also includes covalently attached fluorescer and a quencher molecules located such that when a hairpin is formed, the fluorescer and quencher are in close enough proximity to allow resonance energy transfer between them. This method has the significant short coming that it limits the possible probe sequences to those capable of forming a hairpin structure. Moreover, the kinetics and thermodynamics of probe-target binding will be unfavorably affected by the presence of the hairpin structure.

SUMMARY

The present invention relates generally to our discovery of methods and reagents useful for the combined amplification and hybridization probe detection of amplified nucleic acid target sequence in a single reaction vessel using a single reagent.

An object of our invention is to provide methods and reagents for the amplification and probe detection of amplified target sequences wherein the amplification and probing steps are performed in a combined manner such that no reagent additions are required subsequent to the amplification step.

A further object of our invention is to provide methods and reagents for the amplification and probe detection of amplified target sequences located within cells or tissue sections wherein there is no need to disassemble a containment assembly between the amplification and probing steps.

Another object of our invention is to provide methods and reagents for the amplification and probe detection of amplified target sequences wherein a single reagent mixture is used for both the amplification and probing steps.

A further object of our invention is to provide methods and reagents for the amplification and probing of amplified target sequences located within cells or tissue sections wherein no washing step is required between the amplification and probing steps.

Another object of our invention is to provide a probe composition for use in the above methods that has detectabley different fluorescence characteristics depending on whether it is in a double stranded state, e.g., hybridized to a complementary target sequence, or whether it is in a single stranded state.

Yet another object of our invention is to provide oligonucleotide probes which are resistant to the 5'→3' exonuclease activity of polymerase enzymes.

Another object of our invention is to provide labeled probes in which, at the time of detection, the label is attached to a large, slowly diffusing species, i.e., a species having a size greater than or equal to the size of the probe.

A further object of our invention is to provide probes which do not require hairpin structures in order to provide a differential signal between double stranded and single stranded states.

Another object of our invention is to provide methods and reagents for the amplification and probe detection of amplified target sequences wherein the polymerase is not required to have 5'→3' exonuclease activity.

Yet another object of our invention is to provide methods and reagents for the amplification and probe detection of amplified target sequences wherein multiple sequence sites can be detected within a single target sequence.

Still another object of our invention is to provide various reagent kits useful for the practice of the aforementioned methods.

The foregoing and other objects of the invention are achieved by, in one aspect, an oligonucleotide probe which is made up of an oligonucleotide capable of hybridizing to a target polynucleotide sequence. The oligonucleotide is modified such that the 5' end is rendered impervious to digestion by the 5'→3' exonuclease activity of a polymerase, and the 3' end is rendered impervious to the 3'→5' extension activity of a polymerase. Furthermore, the oligonucleotide probe includes a fluorescer molecule attached to a first end of the oligonucleotide, and a quencher molecule attached to a second end of the oligonucleotide such that the quencher molecule substantially quenches the fluorescence of the fluorescer molecule whenever the oligonucleotide probe is in a single-stranded state and such that the fluorescer is substantially unquenched whenever the oligonucleotide probe is in a double-stranded state. Alternatively, the fluorescer and quencher are separated by at least 18 nucleotides.

In a second aspect, the invention provides a first method for performing combined PCR amplification and hybridization probing. In the method, a target nucleic acid sequence is contacted with PCR reagents, including at least two PCR primers, a polymerase enzyme, and an oligonucleotide probe of the invention as described above. This mixture is then subjected to thermal cycling, the thermal cycling being sufficient to amplify the target nucleic acid sequence specified by the PCR reagents.

In a third aspect, the invention provides a second method for performing combined PCR amplification and hybridization probing wherein the target nucleic acid sequence is contacted with PCR reagents, including at least two PCR primers and a polymerase enzyme substantially lacking any 3'→5' exonuclease activity, and an oligonucleotide probe. The oligonucleotide probe includes a fluorescer molecule attached to a first end of the oligonucleotide and a quencher molecule attached to a second end of the oligonucleotide such that quencher molecule substantially quenches the fluorescence of the fluorescer molecule whenever the oligonucleotide probe is in a single-stranded state and such that the fluorescer is substantially unquenched whenever the oligonucleotide probe is in a double-stranded state. In addition, the 3' end of the probe is rendered impervious to the 3'→5' extension activity of a polymerase. The target nucleic acid sequence, the oligonucleotide probe, and the PCR reagents are subjected to thermal cycling sufficient to amplify the target nucleic acid sequence specified by the PCR reagents.

In one preferred embodiment, rather than requiring the polymerase enzyme to be lacking any 3'→5' exonuclease activity, an exonuclease activity inhibitor is added to the reaction, the inhibitor being sufficient to inhibit the 3'→5' exonuclease activity of the polymerase at a probe hybridization temperature.

In a second preferred embodiment, rather than requiring the polymerase enzyme to be lacking any 3'→5' exonuclease activity, or rather than adding an exonuclease activity inhibitor, the 3'→5' exonuclease activity of the polymerase is deactivated prior to detecting the probe.

DESCRIPTION OF THE PREFERRED EMBODIMENTS

Figure 1:
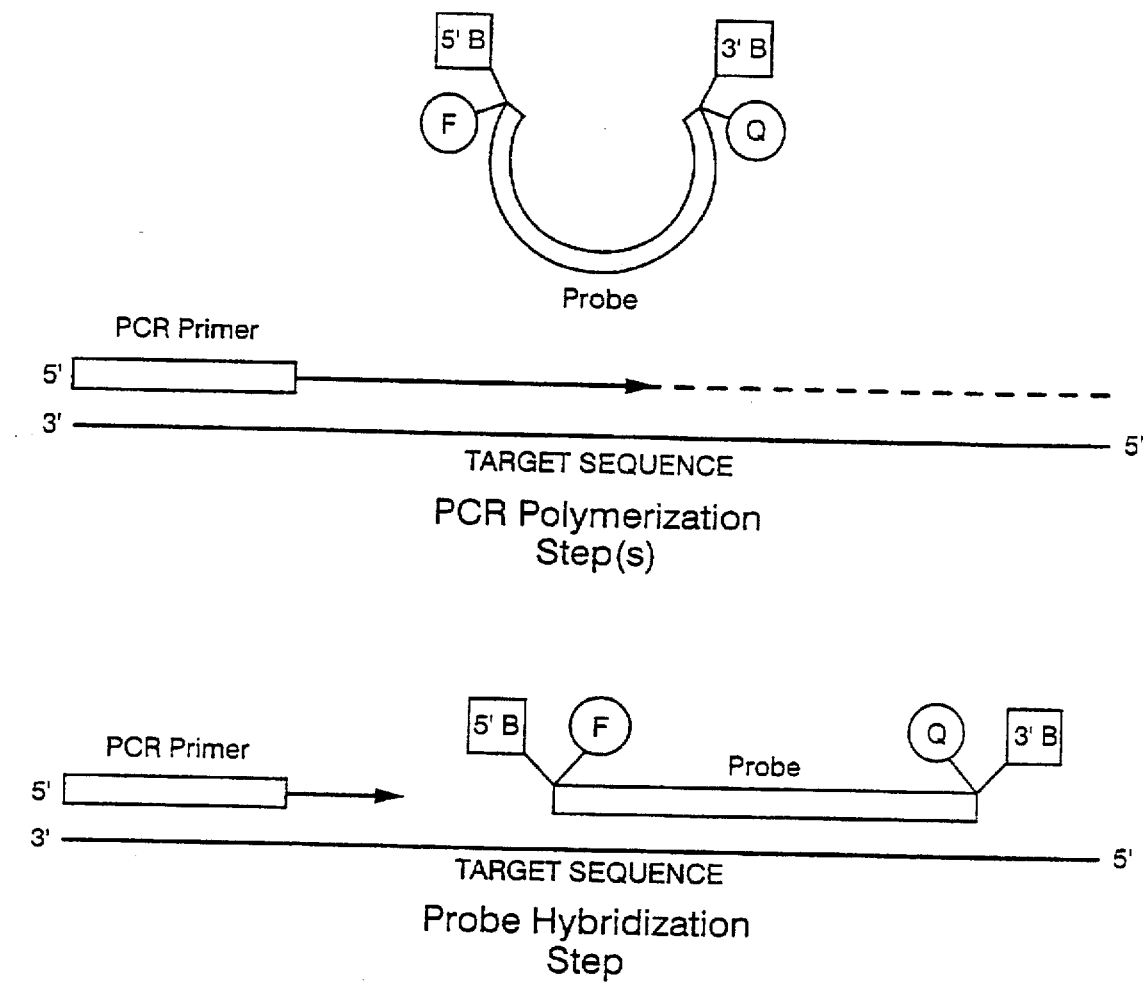
FIG. 1 shows a schematic diagram of a first preferred combined PCR and probe hybridization method wherein a temperature difference between the melting temperature ($T_m$) of the probe and the reaction temperature of the PCR polymerization step is used to prevent the probe from interfering with the PCR polymerization step and digestion of the probe.

Reference will now be made in detail to the preferred embodiments of the invention. While the invention will be described in conjunction with the preferred embodiments, it will be understood that they are not intended to limit the invention to those embodiments. On the contrary, the invention is intended to cover alternatives, modifications, and equivalents which may be included within the invention as defined by the appended claims.

1. PCR and In Situ PCR

As used herein, the term "PCR reagents" refers to the chemicals, apart from the target nucleic acid sequence, needed to perform the PCR process. These chemicals generally consist of five classes of components: (i) an aqueous buffer, (ii) a water soluble magnesium salt, (iii) at least four deoxyribonucleotide triphosphates (dNTPs), (iv) oligonucleotide primers (normally two primers for each target sequence, the sequences defining the 5' ends of the two complementary strands of the double-stranded target sequence), and (v) a polynucleotide polymerase, preferably a DNA polymerase, more preferably a thermostable DNA polymerase, i.e., a DNA polymerase which can tolerate temperatures between 90° C. and 100° C. for a total time of at least 10 min without losing more than about half its activity.

The four conventional dNTPs are thymidine triphosphate (dTTP), deoxyadenosine triphosphate (dATP), deoxycitidine triphosphate (dCTP) and deoxyguanosine triphosphate (dGTP). These conventional triphosphates may be supplemented or replaced by dNTPs containing base analogues which Watson-Crick base pair like the conventional four bases, e.g., deoxyuridine triphosphate (dUTP).

"In situ PCR" refers to PCR amplification performed in fixed cells, such that specific amplified nucleic acid is substantially contained within a cell or subcellular structure which originally contained the target nucleic acid sequence. The cells may be in aqueous suspension or may be part of a tissue sample, e.g., histochemical section, or a cytochemical smear. As used herein, the term "histochemical section" refers to a solid sample of biological tissue which has been frozen or chemically fixed and hardened by embedding in a wax or plastic, sliced into a thin sheet (typically several microns thick), and attached to a solid support, e.g., a microscope slide, and the term "cytochemical smear" refers to a suspension of cells, e.g., blood cells, which has been chemically fixed and attached to a microscope slide. Preferably, the cells will have been rendered permeable to PCR reagents by proteinase digestion, by liquid extraction with a surfactant or organic solvent, or other like permeablization methods.

As used herein, the term "fixed cells" refers to a sample of biological cells which has been chemically treated to strengthen cellular structures, particularly membranes, against disruption by solvent changes, temperature changes, mechanical stress or drying. Cells may be fixed either in suspension our as part of a tissue sample. Cell fixatives generally are chemicals which crosslink the protein constituents of cellular structures, most commonly by reacting with protein amino groups. Preferred fixatives include buffered formalin, 95% ethanol, fomaldehyde, paraformaldehyde, and glutaraldehyde. The permeability of fixed cells can be increased by treatment with proteinases, or with surfactants or organic solvents which dissolve membrane lipids.

2. Oligonucleotide Probes

The term "oligonucleotide" as used herein includes linear oligomers of natural or modified monomers or linkages, including deoxyribonucleotides, ribonucleotides, and the like, capable of specifically binding to a target polynucleotide by way of a regular pattern of monomer-to-monomer interactions, such as Watson-Crick type of base pairing, or the like. Usually monomers are linked by phosphodiester bonds or analogs thereof to form oligonucleotides ranging in size from a few monomeric units, e.g. 3–4, to several tens of monomeric units. Whenever an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphoranilidate, phosphoramidate, and the like.

As used herein, "nucleotide" includes the natural nucleotides, including 2'-deoxy and 2'-hydroxyl forms, e.g. as described in Kornberg and Baker, DNA Replication, 2nd Ed. (Freeman, San Francisco, 1992). "Analogs" in reference to nucleotides includes synthetic nucleotides having modified base moieties and/or modified sugar moieties, e.g. described by Scheit, Nucleotide Analogs (John Wiley, New York, 1980); Uhlman and Peyman, Chemical Reviews, 90: 543–584 (1990), or the like, with the only proviso that they are capable of specific hybridization. Such analogs include synthetic nucleotides designed to enhance binding properties, reduce degeneracy, increase specificity, reduce activity as enzyme substrates, and the like.

Oligonucleotides of the invention can be synthesized by a number of approaches, e.g. Ozaki et al, Nucleic Acids Research, 20: 5205–5214 (1992); Agrawal et al, Nucleic Acids Research, 18: 5419–5423 (1990); or the like. The oligonucleotide probes of the invention are conveniently synthesized on an automated DNA synthesizer, e.g. a Perkin-Elmer (Foster City, Calif.) Model 392 or 394 DNA/RNA Synthesizer, using standard chemistries, such as phosphoramidite chemistry, e.g. disclosed in the following references: Beaucage and Iyer, Tetrahedron, 48: 2223–2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like. Alternative chemistries, e.g. resulting in non-natural backbone groups, such as phosphorothioate, phosphoramidate, and the like, may also be employed provided that the hybridization efficiencies of the resulting oligonucleotides are not adversely affected. Preferably, the oligonucleotide probe is in the range of 15–150 nucleotides in length. More preferably, the oligonucleotide probe is in the range of 18–30 nucleotides in length. The precise sequence and length of an oligonucleotide probe of the invention depends in part on the nature of the target nucleic acid sequence to which it hybridizes. The binding location and length may be varied to achieve appropriate annealing and melting properties for a particular embodiment. Guidance for making such design choices can be found in many of the above-cited references describing the "Taqman" type of assays.

Preferably, the 3' terminal nucleotide of the oligonucleotide probe is rendered incapable of extension by a nucleic acid polymerase. Such blocking may be carried out by the attachment of a fluorescer or quencher molecule to the terminal 3' carbon of the oligonucleotide probe by a linking moiety, or by making the 3'-terminal nucleotide a dideoxynucleotide. Alternatively, the 3' end of the oligonucleotide probe is rendered impervious to the 3'→5' extension activity of a polymerase by including one or more modified internucleotide linkages into the 3' end of the oligonucleotide. Minimally, the 3'-terminal internucleotide linkage must be modified, however, up to all the internucleotide linkages may be modified. Such internucleotide modifications may include phosphorothioate linkeages, e.g., Oligonucleotides and Analogs, Chaps. 4 and 5, IRL Press, New York (1991); methylphosphonate linkages, Oligonucleotides and Analogs, Chap. 6, IRL Press, New York (1991); boranophosphate linkages, e.g., Shaw et al., Methods Mol. Biol. 20: 225–43 (1993); and other like polymerase resistant internucleotide linkages. An alternative method to block 3' extension of the probe is to form an adduct at the 3' end of the probe using mitomycin C or other like antitumor antibiotics, e.g., Basu et al., Biochemistry, 32: 4708–4718 (1993).

In an important aspect of one embodiment of the present invention, the oligonucleotide probe is rendered impervious to degradation by the 5'→3' exonuclease activity of a nucleic acid polymerase. Preferably, the 5' end of the oligonucleotide probe is rendered impervious to digestion by including one or more modified internucleotide linkages into the 5' end of the oligonucleotide. Minimally, the 5'-terminal internucleotide linkage must be modified, however, up to all the internucleotide linkages in the oligonucleotide may be modified. Such internucleotide modifications may include modified linkages of the type used in the synthesis of anti-sense oligonucleotides. Examples of such nuclease resistant linkages include phosphorothioate linkages, e.g., Oligonucleotides and Analogs, Chaps. 4 and 5, IRL Press, New York (1991); methylphosphonate linkages, Oligonucleotides and Analogs, Chap. 6, IRL Press, New York (1991); boranophosphate linkages, e.g., Shaw et al., Methods Mol. Biol. 20: 225–43 (1993); polyamide nucleic acid (PNA) linkages, e.g., Nielsen et al., Science, 254: 1497–1500 (1991), and other like exonuclease resistant linkages. Alternatively, a peptide molecule is be attached to the 5' end of the probe in an manner anaologus to that of Soukchareun et al. in Bioconjugate Chemistry, 6: 43–53 (1995).

In another important aspect of the oligonucleotide probes of the present invention, the probes include fluorescer and quencher molecules attached to the oligonucleotide. As used herein, the terms "quenching" or "fluorescence energy transfer" refer to the process whereby when a fluorescer molecule and a quencher molecule are in close proximity, whenever the fluorescer molecule is excited, a substantial portion of the energy of the excited state nonradiatively transfers to the quencher where it either dissipates nonradiatively or is emitted at a different emission wavelength than that of the fluorescer. It is well known that the efficiency of quenching is a strong function of the proximity of the fluorescer and the quencher, i.e., as the two molecules get closer, the quenching efficiency increases. As quenching is strongly dependent on the physical proximity of the reporter molecule and quencher molecule, it has been assumed that the quencher and reporter molecules must be attached to the probe within a few nucleotides of one another, usually with a separation of about 6–16 nucleotides, e.g. Lee et al. Nucleic Acids Research, 21: 3761–3766 (1993); Mergny et al, Nucleic Acids Research, 22: 920–928 (1994); Cardullo et al, Proc. Natl. Acad. Sci., 85: 8790–8794 (1988); Clegg et al, Proc. Natl. Acad. Sci., 90: 2994–2998 (1993); Ozaki et al, Nucleic Acids Research, 20: 5205–5214 (1992); and the like. Typically, this separation is achieved by attaching one member of a reporter-quencher pair to the 5' end of the probe and the other member to a base 6–16 nucleotides away.

However, it has been recognized as part of the present invention that by placing the fluorescer and quencher molecules at seemingly remote locations on the oligonucleotide, differential quenching can be seen between the single stranded state and the double stranded state, i.e., hybridized state, of the oligonucleotide probe, e.g., Bagwell et al., Nucleic Acids Research, 22(12): 2424–2425 (1994); Bagwell, EP 0 601 889 A2. The fluorescence signals can differ by as much as a factor of 20 between the single stranded and double stranded states when the fluorescer and quencher are separated by 20 bases. This effect is most probably due to the fact that in the single stranded state, the oligonucleotide exists as a flexible random coil structure which allows the ends of the oligonucleotide to be in close proximity, while, in the double stranded state, the oligonucleotide exists as a rigid, extended structure which separates the fluorescer and quencher. Thus, using this arrangement, one sees relatively efficient quenching of the fluorescer when the oligonucleotide probe is in the single stranded or unhybridized state and relatively inefficient quenching of the fluorescer when the oligonucleotide probe is in the double stranded or hybridized state.

Preferably, fluorescer molecules are fluorescent organic dyes derivatized for attachment to the terminal 3' carbon or terminal 5' carbon of the probe via a linking moiety. Preferably, quencher molecules are also organic dyes, which may or may not be fluorescent, depending on the embodiment of the invention. For example, in a preferred embodiment of the invention, the quencher molecule is fluorescent. Generally, whether the quencher molecule is fluorescent or simply releases the transferred energy from the fluorescer by non-radiative decay, the absorption band of the quencher should substantially overlap the fluorescent emission band of the fluorescer molecule. Non-fluorescent quencher molecules that energy from excited fluorescer molecules, but which do not release the energy radiatively, are referred to herein as chromogenic molecules.

There is a great deal of practical guidance available in the literature for selecting appropriate fluorescer-quencher pairs for particular probes, as exemplified by the following references: Clegg (cited above); Wu et al., Anal. Biochem., 218: 1–13 (1994). Pesce et al, editors, Fluorescence Spectroscopy (Marcel Dekker, New York, 1971); White et al, Fluorescence Analysis: A Practical Approach (Marcel Dekker, New York, 1970); and the like. The literature also includes references providing exhaustive lists of fluorescent and chromogenic molecules and their relevant optical properties for choosing fluorescer-quencher pairs, e.g. Berlman, Handbook of Fluorescence Sprectra of Aromatic Molecules, 2nd Edition (Academic Press, New York, 1971); Griffiths, Colour and Consitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); and the like. Further, there is extensive guidance in the literature for derivatizing fluorescer and quencher molecules for covalent attachment via common reactive groups that can be added to an oligonucleotide, as exemplified by the following references: Haugland (cited above); Ullman et al, U.S. Pat. No. 3,996,345; Khanna et al, U.S. Pat. No. 4,351,760; and the like.

Exemplary fluorescer-quencher pairs may be selected from xanthene dyes, including fluoresceins, and rhodamine dyes. Many suitable forms of these compounds are widely available commercially with substituents on their phenyl moieties which can be used as the site for bonding or as the bonding functionality for attachment to an oligonucleotide. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl-6-naphthalene sulfonate. Other dyes include 3-phenyl-7-isocyanatocoumarin, acridines, such as 9-isothiocyanatoacridine acridine orange; N-(p-(2-benzoxazolyl)phenyl)maleimide; benzoxadiazoles, stilbenes, pyrenes, and the like.

Preferably, fluorescer and quencher molecules are selected from fluorescein and rhodamine dyes. These dyes and appropriate linking methodologies for attachment to oligonucleotides are described in many references, e.g. Khanna et al (cited above); Marshall, Histochemical J., 7: 299–303 (1975); Mechnen et al, U.S. Pat. No. 5,188,934; Menchen et al, European patent application 87310256.0; and Bergot et al, International application PCT/US90/05565. The latter four documents are hereby incorporated by reference.

There are many linking moieties and methodologies for attaching fluorescer or quencher molecules to the 5' or 3' termini of oligonucleotides, as exemplified by the following references: Eckstein, editor, Oligonucleotides and Analogues: A Practical Approach (IRL Press, Oxford, 1991); Zuckerman et al, Nucleic Acids Research, 15: 5305–5321 (1987)(3' thiol group on oligonucleotide); Sharma et al, Nucleic Acids Research, 19: 3019 (1991)(3' sulfhydryl); Giusti et al, PCR Methods and Applications, 2: 223–227 (1993) and Fung et al, U.S. Pat. No. 4,757,141 (5' phosphoamino group via Aminolink™ II available from Applied Biosystems, Foster City, Calif.); Stabinsky, U.S. Pat. No. 4,739,044 (3' aminoalkylphosphoryl group); Agrawal et al, Tetrahedron Letters, 31: 1543–1546 (1990)(attachment via phosphoramidate linkages); Sproat et al, Nucleic Acids Research, 15: 4837 (1987)(5' mercapto group); Nelson et al, Nucleic Acids Research, 17: 7187–7194 (1989)(3' amino group); and the like.

Preferably, commercially available linking moieties are employed that can be attached to an oligonucleotide during synthesis, e.g. available from Clontech Laboratories (Palo Alto, Calif.).

Rhodamine and fluorescein dyes are also conveniently attached to the 5' hydroxyl of an oligonucleotide at the conclusion of solid phase synthesis by way of dyes derivatized with a phosphoramidite moiety, e.g. Woo et al, U.S. Pat. No. 5,231,191; and Hobbs, Jr. U.S. Pat. No. 4,997,928.

3. Combined PCR Amplification and Probe Hybridization

There are three key issues which must be addressed when performing combined PCR and probe hybridization assays: (i) the oligonucleotide probe should not block or otherwise interfere with the PCR polymerization step thereby reducing the stepwise efficiency of the amplification, where as used herein, the term "polymerization step" refers to the step in the PCR process in which the primers are extended from their 3' ends by incorporation of nucleotide bases by a polymerase-mediated reaction; (ii) the oligonucleotide probe must not be digested by the 5'→3' exonuclease activity of the polymerase enzyme; and (iii) the probe should be incapable 3'→5' extension by the polymerase.

In one preferred embodiment of the present invention, the probe is protected from interfering with the PCR polymerization step by designing the probe such that its melting temperature is above the temperature of the PCR polymerization step. As used herein, the term "melting temperature" is defined as a temperature at which half of the probe is hybridized to a target sequence, i.e., in a double stranded state, and half is in unhybridized, i.e., in a single stranded state. Preferably, the melting temperature of the probe is between 40° C. and 55° C., and the melting temperature of the PCR primers is between 55° C. and 70° C.

Referring to FIG. 1, during the PCR polymerization step, the probe is unhybridized, i.e., in a single stranded state, and thereby quenched. Moreover, because the probe is not bound to the target sequence, the PCR polymerization can proceed without interference from the probe. Next, during the hybridization step, the temperature is reduced to a hybridization temperature, preferably a temperature at or below the $T_m$ of the probe, causing the probe to hybridize to the target. The hybridization of the probe causes a reduction in the amount of quenching, resulting in a measurable signal which is indicative of probe hybridization to the target sequence, such signal also providing quantitative information as to the mount of target sequence present. During the hybridization step, the probe will not be digested by the exonuclease activity of the polymerase because, as discussed above, the probe has been designed to be impervious to the 5'→3' exonuclease activity of the polymerase.

In a variation on the above described $T_m$ mediated combined PCR and probe hybridization method, rather than using a probe which is impervious to the 5'→3' exonuclease activity of the polymerase, digestion of the probe during the hybridization step is prevented by using a polymerase which lacks a 5'→3' exonuclease activity. Examples of such 5'→3' minus polymerases include DNA polymerase I Klenow fragment, T4 DNA polymerase, and T7 DNA polymerase, and other like 5'→3' exonuclease minus DNA polymerases, e.g., Amershan Life Science, Inc., Arlington Heights, Ill.

In a second variation of the above described $T_m$ mediated combined PCR and probe hybridization method, rather than using a probe which is impervious to the 5'→3' exonuclease activity of the polymerase or using an exonuclease-minus polymerase to protect the probe from exonuclease digestion, the polymerase is rendered inactive with respect to its exonuclease activity during the hybridization step. Such inactivation can be achieved in a number of ways including (i) introducing a temperature sensitive inhibitor into the reaction which will inhibit the 5'→3' exonuclease activity of the polymerase at the hybridization temperature, e.g., a solid adsorbent, a specific antibody molecule, or other like reversible or irreversible polymerase inhibitors; (ii) using a polymerase whose activity is greatly reduced at the hybridization temperature; or (iii) introducing an enzyme deactivation step prior to the hybridization step which irreversibly kills the polymerase enzyme, i.e., an extended period at high temperature.

Figure 2:
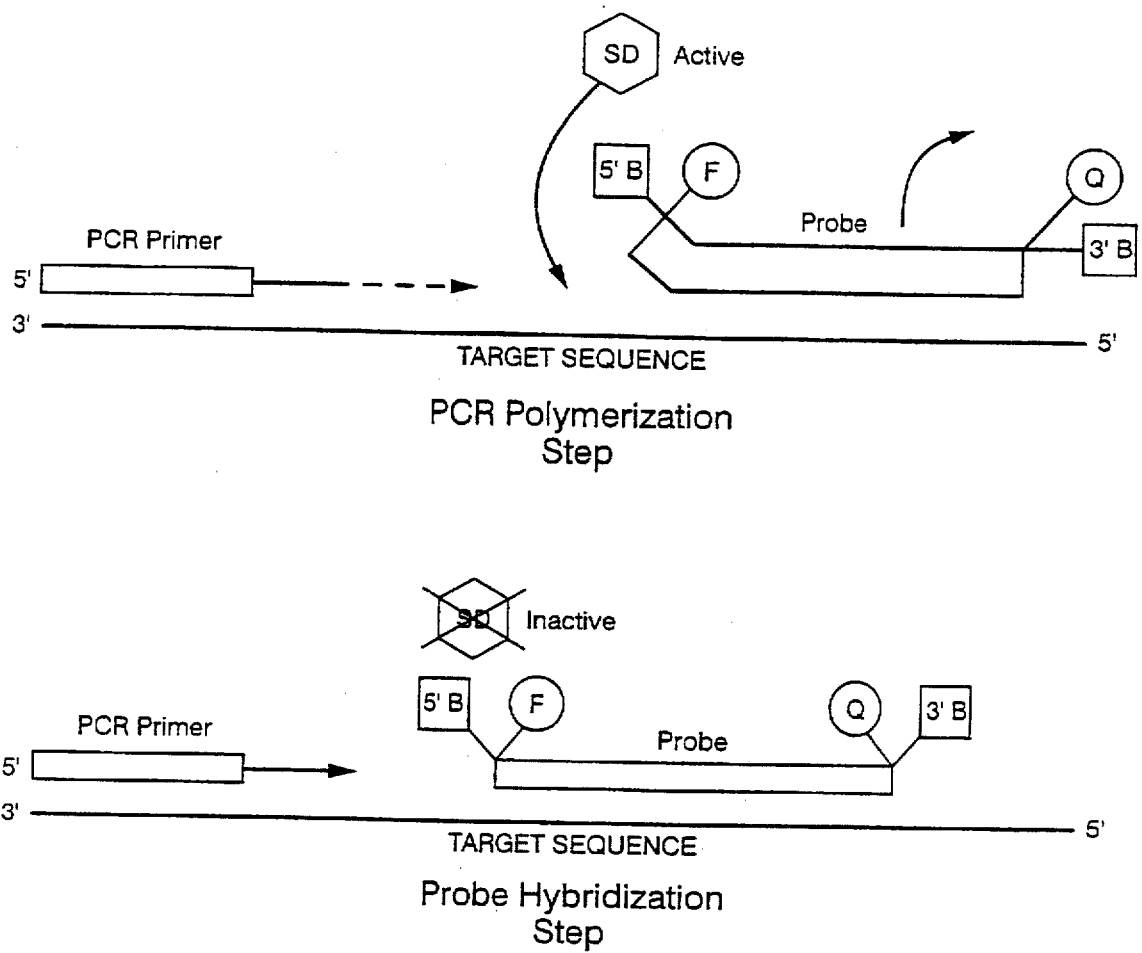
FIG. 2 shows a schematic diagram of a second preferred combined PCR and probe hybridization method wherein a strand displacer is used to prevent the probe from interfering with the PCR polymerization step and digestion of the probe.

In a second preferred embodiment of the present invention, the probe is prevented from interfering with the PCR polymerization step by including a strand displacer into the reaction, where, as used herein, the term "strand displacer" refers to an agent capable of causing the displacement of an oligonucleotide probe from a target to which it is hybridized, e.g., a DNA helicase, e.g., Howard et al., Proc. Natl. Acad. Sci. USA 91: 12031–12035 (1994), or a single-stranded binding protein, E. G. Zijderveld, Journal of Virology 68(2): 1158–1164 (1994). Referring to FIG. 2, in this embodiment, during the polymerization step, the strand displacer displaces the probe from the template strand thereby allowing the polymerization step to proceed without interference from the probe. Then, in order to allow hybridization of the probe during the hybridization step, the strand displacer is rendered inactive. Such inactivation can be achieved in a number of ways including those described above with reference to inactivation of exonuclease activity. Generally, the strand displacement activity of a strand displacer is higher for longer oligonucleotide duplexes, thus, the PCR primers themselves are not susceptible to strand displacement during the PCR reaction.

4. Examples

The Invention will be further clarified by a consideration of the following examples, which are intended to be purely exemplary of the invention.

EXAMPLE 1

Comparison of Fluorescence Emissions of Probes in Single Stranded and Double Stranded States Linker arm nucleotide ("LAN") phosphoramidite was obtained from Glen Research. Standard DNA phosphoramidites, 6-carboxyfluorescein ("6-FAM") phosphoramidite, 6-carboxytetramethylrhodamine succinimidyl ester ("TAMRA NHS ester"), and Phosphalink™ for attaching a 3' blocking phosphate were obtained from Perkin-Elmer, Applied Biosystems Division. Oligonucleotide synthesis was performed on a model 394 DNA Synthesizer (Applied Biosystems). Oligonucleotides were purified using Oligo Purification Cartridges (Applied Biosystems).

Doubly labeled probes were synthesized with 6-FAM-labeled phosphoramidite at the 5' end, LAN replacing one of the T's in the oligonucleotide sequence, and Phosphalink™ at the 3' end. Following deprotection and ethanol precipitation, TAMRA NHS ester was coupled to the LAN-containing oligonucleotide in 250 mM Na-bicarbonate buffer (pH 9.0) at room temperature. Unreacted dye was removed by passage over a PD-10 Sephadex column. Finally, the doubly labeled probe was purified by preparative HPLC using standard protocols.

The oligonucleotide sequences of the probes and their complements are shown in Table 1. As used herein, the term "complement" refers to an oligonucleotide sequence which is capable of hybridizing specifically with a probe sequence.

TABLE 1

| Probe/Complement | SEQ ID NO: | Sequence |
|---|---|---|
| 1 | SEQ ID NO: 1 | ATGCCCTCCCCCATGCCATCCTGCGT |
| 1 (Complement) | SEQ ID NO: 2 | AGACGCAGGATGGCATGGGGGAGGGCATAC |
| 2 | SEQ ID NO: 3 | CGCCCTGGACTTCGAGCAAGAGAT |
| 2 (Complement) | SEQ ID NO: 4 | CCATCTCTTGCTCGAAGTCCAGGGCGAC |
| 3 | SEQ ID NO: 5 | TCGCATTACTGATCGTTGCCAACCAGT |
| 3 (Complement) | SEQ ID NO: 6 | GTACTGGTTGGCAACGATCAGTAATGCGATG |
| 4 | SEQ ID NO: 7 | CGGATTTGCTGGTATCTATGACAAGGAT |
| 4 (Complement) | SEQ ID NO: 8 | TTCATCCTTGTCATAGATACCAGCAAATCCG |

Four pairs of probes were studied. For each pair, one probe has TAMRA attached to an internal nucleotide, the other has TAMRA attached to the 3' end nucleotide, and both probes have 6-FAM attached to the 5' end. To measure the fluorescence of the probes in a single stranded state, fluorescence emissions at 518 nm were measured using solutions containing a final concentration of 50 nM probe, 10 mM Tris-HCl (pH 8.3), 50 mM KCl, and 10 mM MgCl$_2$. measure the fluorescence of the probes in double stranded state, the solutions additionally contained 100 mM complement oligonucleotide. Before addition of the MgCl$_2$, 120 μl of each sample was heated at 95° C. for 5 min. Following the addition of 80 μl of 25 mm MgCl$_2$, each sample was allowed to cool to room temperature and the fluorescence emissions were measured. Reported values are the average of three measurements. Table 2 gives the results of fluorescence measurements of the indicated probes in single and double stranded states. As can be seen from the data in Table 2, for probes having the fluorescer and quencher at opposite ends of the oligonucleotide, hybridization caused a dramatic increase in the degree of differential quenching over that seen when the fluorescer and quencher were closer together. For longer probes, we would expect that there exists an optimum separation between the fluorescer and the quencher such that rather than placing the fluorescer and quencher at oppisite ends, they are both located internally but separated by some optimum distance.

TABLE 2

| Probe | TAMRA Location[a] | Differential Quenching[b] |
|---|---|---|
| 1 | 7 | 2.5 |
| 1 | 26 | 11.8 |
| 2 | 6 | 3.7 |
| 2 | 24 | 19.2 |
| 3 | 7 | 2.0 |
| 3 | 27 | 8.0 |
| 4 | 10 | 5.3 |
| 4 | 28 | 14.0 |

[a]The TAMRA location is expressed as the number of nucleotides from the 5' end of the oligonucleotide in a 5' to 3' direction.
[b]Differential quenching is defined as the fluorescence emission intensity of the probe in the double stranded state divided by the fluorescence emission intensity of the probe in the single stranded state.

Although only a few embodiments have been described in detail above, those having ordinary skill in the molecular biology art will clearly understand that many modifications and variations are possible in the preferred embodiments without departing from the teachings thereof.

---

We claim:

1. A method for performing combined PCR amplification and hybridization probing comprising the steps of:

contacting a target nucleic acid with PCR reagents, including at least two PCR primers and a polymerase enzyme, and an oligonucleotide probe comprising:

an oligonucleotide capable of hybridizing to a target nucleic acid;

a fluorescer molecule attached to a first end of the oligonucleotide;

a quencher molecule attached to a second end of the oligonucleotide such that the quencher molecule substantially quenches the fluorescer molecule whenever the oligonucleotide probe is in a single-stranded state and such that the fluorescer is substantially unquenched whenever the oligonucleotide probe is hybridized to the target nucleic acid;

a 5' end which is rendered impervious to digestion by the 5'→3' exonuclease activity of a polymerase; and a 3' end which is rendered impervious to the 5'→3' extension activity of the polymerase; and subjecting the target nucleic acid, the oligonucleotide probe, and the PCR reagents to thermal cycling, including a polymerization step, the thermal cycling being sufficient to amplify the target nucleic acid specified by the PCR reagents.

2. The method of claim 1 further comprising the step of measuring the extent of fluorescence quenching of the oligonucleotide probe, such measurement being performed subsequent to thermocycling and at a probe hybridization temperature.

3. The method of claim 1 wherein the target nucleic acid sequence is located within one or more fixed cells.

4. The method of claim 3 further comprising the step of measuring the extent of fluorescence quenching of the oligonucleotide probe at a probe hybridization temperature in a manner which locates the probe within the individual cells originally containing the target nucleic acid sequence.

5. The method of claim 3 wherein the fixed cells, the PCR reagents, and the oligonucleotide probe are located in a containment assembly.

6. The method of claim 2 wherein the probe hybridization temperature is less than or equal to the temperature of the polymerization step of the thermocycling.

7. The method of claim 2 further comprising the step of adding a strand displacer prior to thermal cycling for preventing the oligonucleotide probe from blocking the 5'→3' extension of an upstream PCR primer during the polymerization step while not substantially displacing the PCR primer.

8. The method of claim 7 further comprising a strand displacer deactivation step subsequent to thermocycling for deactivating the strand displacement activity of the strand displacer.

9. The method of claim 1 further comprising the step of adding a strand displacer prior to thermal cycling for preventing the oligonucleotide probe from blocking the 5'→3' extension of an upstream PCR primer.

10. The method of claim 9 wherein the strand displacer is a helicase.

* * * * *